(12) United States Patent
Schewe et al.

(10) Patent No.: US 8,455,088 B2
(45) Date of Patent: *Jun. 4, 2013

(54) SPUN NANOFIBER, MEDICAL DEVICES, AND METHODS

(75) Inventors: Scott R. Schewe, Eden Prairie, MN (US); Michele L. Zoromski, Minneapolis, MN (US); Liliana L. Atanasoska, Edina, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 883 days.

This patent is subject to a terminal disclaimer.

(21) Appl. No.: 11/318,027

(22) Filed: Dec. 23, 2005

(65) Prior Publication Data

US 2007/0144124 A1    Jun. 28, 2007

(51) Int. Cl.
*C07F 7/02* (2006.01)

(52) U.S. Cl.
USPC .................. 428/292.1; 428/297.4; 428/297.7; 428/903; 524/188; 524/261; 524/262; 524/265; 524/588; 524/589; 977/788

(58) Field of Classification Search
USPC ............ 977/700–963; 428/364, 292.1, 297.4, 428/297.7, 903; 524/188, 261, 262, 265, 524/588, 589
See application file for complete search history.

(56) References Cited

U.S. PATENT DOCUMENTS

| | | | |
|---|---|---|---|
| 2,928,858 A | 3/1960 | Morehouse |
| 4,043,331 A | 8/1977 | Martin et al. |
| 4,780,337 A | 10/1988 | Seyferth et al. |
| 5,180,757 A | 1/1993 | Lucey |
| 5,254,744 A | 10/1993 | Neumer |
| 5,316,695 A | 5/1994 | Wilkes et al. |
| 5,389,170 A | 2/1995 | Brady et al. |
| 5,486,565 A | 1/1996 | Gentle et al. |
| 5,665,823 A | 9/1997 | Saxena et al. |
| 5,681,872 A | 10/1997 | Erbe |
| 5,716,565 A | 2/1998 | Stangle et al. |
| 5,767,218 A | 6/1998 | Becker et al. |
| 5,834,007 A | 11/1998 | Kubota |
| 5,854,298 A | 12/1998 | McNay et al. |
| 5,866,027 A | 2/1999 | Frank et al. |
| 5,871,777 A | 2/1999 | Ducheyne et al. |
| 5,874,109 A | 2/1999 | Ducheyne et al. |
| 5,914,356 A | 6/1999 | Erbe |
| 6,001,522 A | 12/1999 | Woo et al. |
| 6,039,897 A | 3/2000 | Lochhead et al. |
| 6,060,026 A | 5/2000 | Goldstein |
| 6,069,259 A | 5/2000 | Crivello |
| 6,086,668 A | 7/2000 | Farneth et al. |
| 6,099,965 A | 8/2000 | Tennent et al. |
| 6,103,033 A | 8/2000 | Say et al. |
| 6,120,676 A | 9/2000 | Heller et al. |
| 6,131,580 A | 10/2000 | Ratner et al. |
| 6,134,461 A | 10/2000 | Say et al. |
| 6,143,164 A | 11/2000 | Heller et al. |
| 6,162,530 A | 12/2000 | Xiao et al. |
| 6,162,611 A | 12/2000 | Heller et al. |
| 6,175,752 B1 | 1/2001 | Say et al. |
| 6,210,790 B1 | 4/2001 | Crivello |
| 6,214,530 B1 | 4/2001 | Morrison et al. |
| 6,251,260 B1 | 6/2001 | Heller et al. |
| 6,258,974 B1 | 7/2001 | Wellinghoff et al. |
| 6,271,292 B1 | 8/2001 | Mager et al. |
| 6,280,838 B1 | 8/2001 | Bernards et al. |
| 6,281,322 B1 | 8/2001 | Groth et al. |
| 6,284,478 B1 | 9/2001 | Heller et al. |
| 6,299,757 B1 | 10/2001 | Feldman et al. |
| 6,303,290 B1 | 10/2001 | Liu et al. |
| 6,323,146 B1 | 11/2001 | Pugh et al. |
| 6,329,161 B1 | 12/2001 | Heller et al. |
| 6,338,790 B1 | 1/2002 | Feldman et al. |
| 6,361,660 B1 | 3/2002 | Goldstein |
| 6,368,535 B1 | 4/2002 | Katsoulis et al. |
| 6,382,526 B1 | 5/2002 | Reneker et al. |
| 6,391,999 B1 | 5/2002 | Crivello |
| 6,410,765 B1 | 6/2002 | Wellinghoff et al. |
| 6,413,538 B1 | 7/2002 | Garcia et al. |
| 6,432,866 B1 | 8/2002 | Tennent et al. |
| 6,448,331 B1 | 9/2002 | Ioka et al. |
| 6,458,386 B1 | 10/2002 | Schacht et al. |
| 6,461,496 B1 | 10/2002 | Feldman et al. |
| 6,465,387 B1 | 10/2002 | Pinnavaia et al. |
| 6,478,994 B1 | 11/2002 | Sneddon et al. |
| 6,479,565 B1 | 11/2002 | Stanley |
| 6,484,046 B1 | 11/2002 | Say et al. |
| 6,506,921 B1 | 1/2003 | Wilkes et al. |
| 6,514,718 B2 | 2/2003 | Heller et al. |
| 6,517,802 B1 | 2/2003 | Xiao et al. |
| 6,520,425 B1 | 2/2003 | Reneker |
| 6,531,704 B2 | 3/2003 | Yadav et al. |
| 6,548,590 B1 | 4/2003 | Koloski et al. |

(Continued)

FOREIGN PATENT DOCUMENTS

| | | |
|---|---|---|
| DE | 102 39 762 A1 | 3/2004 |
| EP | 0297176 A1 | 4/1989 |

(Continued)

OTHER PUBLICATIONS

XP-001216262 Charbouillot, Y., et al. "Aminosils: New Solid State Protonic Materials by the Sol-Gel Process," Journal of Non-Crystalline Solids, vol. 103, pp. 325-330 (1988).

(Continued)

*Primary Examiner* — Elizabeth Cole
(74) *Attorney, Agent, or Firm* — Brooks, Cameron & Huebsch, PLLC

(57) ABSTRACT

The present disclosure relates to compounds from which nanofibers can be produced, the resulting nanofibers produced from the compounds, and nanofiber reinforced polymers prepared using the nanofibers and a polymer. The compounds used in forming the nanofibers include chemical linkage moieties that are capable of forming non-covalent bonds with portions of the polymer so as to form the nanofiber reinforced polymers. The nanofiber reinforced polymers are useful as biomaterials in medical devices.

20 Claims, No Drawings

U.S. PATENT DOCUMENTS

| | | |
|---|---|---|
| 6,551,494 B1 | 4/2003 | Heller et al. |
| 6,555,175 B2 | 4/2003 | Johnson |
| 6,559,631 B1 | 5/2003 | Balch et al. |
| 6,565,509 B1 | 5/2003 | Say et al. |
| 6,566,456 B1 | 5/2003 | Yang et al. |
| 6,576,101 B1 | 6/2003 | Heller et al. |
| 6,585,992 B2 | 7/2003 | Pugh et al. |
| 6,589,457 B1 | 7/2003 | Li et al. |
| 6,591,125 B1 | 7/2003 | Buse et al. |
| 6,592,745 B1 | 7/2003 | Feldman et al. |
| 6,599,631 B2 | 7/2003 | Kambe et al. |
| 6,616,819 B1 | 9/2003 | Liamos et al. |
| 6,618,934 B1 | 9/2003 | Feldman et al. |
| 6,620,905 B1 | 9/2003 | Musa |
| 6,634,576 B2 | 10/2003 | Verhoff et al. |
| 6,645,644 B1 | 11/2003 | Schwartz et al. |
| 6,649,083 B1 | 11/2003 | Pinnavaia et al. |
| 6,649,713 B2 | 11/2003 | Tang et al. |
| 6,654,625 B1 | 11/2003 | Say et al. |
| 6,667,016 B1 | 12/2003 | Meyer et al. |
| 6,673,458 B2 | 1/2004 | Mager et al. |
| 6,680,016 B2 | 1/2004 | Wang et al. |
| 6,695,617 B1 | 2/2004 | Wellinghoff et al. |
| 6,695,992 B2 | 2/2004 | Reneker |
| 6,696,585 B1 | 2/2004 | Wellinghoff et al. |
| 6,713,011 B2 | 3/2004 | Chu et al. |
| 6,743,936 B1 | 6/2004 | Wellinghoff et al. |
| 6,749,740 B2 | 6/2004 | Liamos et al. |
| 6,753,454 B1 | 6/2004 | Smith et al. |
| 6,759,431 B2 | 7/2004 | Hunter et al. |
| 6,790,528 B2 | 9/2004 | Wendorff et al. |
| 6,812,268 B2 | 11/2004 | Schneider et al. |
| 6,825,260 B2 | 11/2004 | Sievers et al. |
| 6,828,404 B2 | 12/2004 | Crivello |
| 6,838,005 B2 | 1/2005 | Tepper et al. |
| 6,841,601 B2 | 1/2005 | Serpico et al. |
| 6,846,493 B2 | 1/2005 | Pugh et al. |
| 6,869,938 B1 | 3/2005 | Schwartz et al. |
| 6,881,448 B1 | 4/2005 | Hattori |
| 6,881,490 B2 | 4/2005 | Kambe et al. |
| 6,881,551 B2 | 4/2005 | Heller et al. |
| 6,884,628 B2 | 4/2005 | Hubbell et al. |
| 6,906,003 B2 | 6/2005 | Struthers et al. |
| 6,916,640 B2 | 7/2005 | Yu et al. |
| 6,942,518 B2 | 9/2005 | Liamos et al. |
| 6,955,771 B2 | 10/2005 | Ryang |
| 6,973,706 B2 | 12/2005 | Say et al. |
| 6,975,893 B2 | 12/2005 | Say et al. |
| 7,003,340 B2 | 2/2006 | Say et al. |
| 7,013,965 B2 | 3/2006 | Zhong et al. |
| 7,014,803 B2 | 3/2006 | Perez et al. |
| 7,470,466 B2 | 12/2008 | Ippoliti et al. |
| 7,674,864 B2 * | 3/2010 | Zoromski et al. ............ 525/403 |
| 2001/0000889 A1 | 5/2001 | Yadav et al. |
| 2002/0042657 A1 | 4/2002 | Pugh et al. |
| 2002/0047058 A1 | 4/2002 | Verhoff et al. |
| 2002/0094569 A1 | 7/2002 | Yu et al. |
| 2002/0123592 A1 | 9/2002 | Zhang et al. |
| 2002/0128234 A1 | 9/2002 | Hubbell et al. |
| 2002/0161101 A1 | 10/2002 | Carroll et al. |
| 2002/0192289 A1 | 12/2002 | Zheng et al. |
| 2002/0197456 A1 | 12/2002 | Pope |
| 2002/0197467 A1 | 12/2002 | Johnson |
| 2003/0003160 A1 | 1/2003 | Pugh et al. |
| 2003/0024277 A1 | 2/2003 | Costa et al. |
| 2003/0044802 A1 | 3/2003 | Sayler et al. |
| 2003/0055139 A1 | 3/2003 | Cruse |
| 2003/0059742 A1 | 3/2003 | Webster et al. |
| 2003/0062263 A1 | 4/2003 | Stanford et al. |
| 2003/0064086 A1 | 4/2003 | Carrion et al. |
| 2003/0065121 A1 | 4/2003 | Lee |
| 2003/0118887 A1 | 6/2003 | Serpico et al. |
| 2003/0127393 A1 | 7/2003 | Tepper et al. |
| 2003/0129654 A1 | 7/2003 | Ravkin et al. |
| 2003/0137069 A1 | 7/2003 | Reneker |
| 2003/0158351 A1 | 8/2003 | Smith, Jr. et al. |
| 2003/0199615 A1 | 10/2003 | Chaput et al. |
| 2003/0207326 A1 | 11/2003 | Su et al. |
| 2003/0208248 A1 | 11/2003 | Carter et al. |
| 2003/0228415 A1 | 12/2003 | Bi et al. |
| 2003/0228682 A1 | 12/2003 | Lakowicz et al. |
| 2003/0236573 A1 | 12/2003 | Evans et al. |
| 2004/0001959 A1 | 1/2004 | Schwartz et al. |
| 2004/0009598 A1 | 1/2004 | Hench et al. |
| 2004/0018961 A1 | 1/2004 | Stupp et al. |
| 2004/0023048 A1 | 2/2004 | Schwartz et al. |
| 2004/0023253 A1 | 2/2004 | Kunwar et al. |
| 2004/0034434 A1 | 2/2004 | Evans et al. |
| 2004/0053060 A1 | 3/2004 | Roziere et al. |
| 2004/0064193 A1 | 4/2004 | Evans et al. |
| 2004/0115239 A1 | 6/2004 | Shastri et al. |
| 2004/0121451 A1 | 6/2004 | Moritz et al. |
| 2004/0126649 A1 | 7/2004 | Chen et al. |
| 2004/0127987 A1 | 7/2004 | Evans et al. |
| 2004/0137582 A1 | 7/2004 | Dordick et al. |
| 2004/0138758 A1 | 7/2004 | Evans et al. |
| 2004/0146560 A1 | 7/2004 | Whiteford et al. |
| 2004/0150331 A1 | 8/2004 | Okubo et al. |
| 2004/0171779 A1 | 9/2004 | Matyjaszewski et al. |
| 2004/0172061 A1 | 9/2004 | Yoshioka et al. |
| 2004/0206448 A1 | 10/2004 | Dubrow |
| 2004/0217010 A1 | 11/2004 | Hu et al. |
| 2004/0222080 A1 | 11/2004 | Tour et al. |
| 2004/0222081 A1 | 11/2004 | Tour et al. |
| 2004/0249006 A1 | 12/2004 | Gleason et al. |
| 2004/0249082 A1 | 12/2004 | Zhang et al. |
| 2004/0250950 A1 | 12/2004 | Dubrow |
| 2004/0258726 A1 | 12/2004 | Stupp et al. |
| 2005/0006800 A1 | 1/2005 | Mountziaris et al. |
| 2005/0010001 A1 | 1/2005 | Reddy et al. |
| 2005/0014283 A1 | 1/2005 | Matsuura et al. |
| 2005/0019784 A1 | 1/2005 | Su et al. |
| 2005/0032246 A1 | 2/2005 | Brennan et al. |
| 2005/0038220 A1 | 2/2005 | Shin et al. |
| 2005/0038498 A1 | 2/2005 | Dubrow et al. |
| 2005/0043775 A1 | 2/2005 | John et al. |
| 2005/0043894 A1 | 2/2005 | Fernandez |
| 2005/0046086 A1 | 3/2005 | Lee et al. |
| 2005/0053542 A1 | 3/2005 | Harutyunyan |
| 2005/0059755 A1 | 3/2005 | Schneider et al. |
| 2005/0069573 A1 | 3/2005 | Cohn et al. |
| 2005/0069718 A1 | 3/2005 | Voss-Kehl et al. |
| 2005/0100578 A1 | 5/2005 | Schmid et al. |
| 2005/0123611 A1 | 6/2005 | Barbe et al. |
| 2005/0124243 A1 | 6/2005 | Patel et al. |
| 2005/0129580 A1 | 6/2005 | Swinehart et al. |
| 2005/0158763 A1 | 7/2005 | Ivanisevic et al. |
| 2005/0163821 A1 | 7/2005 | Sung et al. |
| 2005/0175880 A1 | 8/2005 | Cho et al. |
| 2005/0176843 A1 | 8/2005 | Burtscher et al. |
| 2005/0192367 A1 * | 9/2005 | Ou et al. ..................... 521/64 |
| 2005/0201987 A1 | 9/2005 | Pirhonen et al. |
| 2005/0208100 A1 | 9/2005 | Weber et al. |
| 2005/0215718 A1 | 9/2005 | Rajagopalan et al. |
| 2005/0215728 A1 | 9/2005 | Cao et al. |
| 2005/0220891 A1 | 10/2005 | Yu et al. |
| 2005/0221072 A1 | 10/2005 | Dubrow et al. |
| 2005/0226904 A1 | 10/2005 | Choi et al. |
| 2005/0228140 A1 | 10/2005 | Rajagopalan et al. |
| 2005/0230659 A1 | 10/2005 | Hampden-Smith et al. |
| 2005/0231773 A1 | 10/2005 | Sasa et al. |
| 2005/0237483 A1 | 10/2005 | Phelan |
| 2005/0238080 A1 | 10/2005 | Wolkin et al. |
| 2005/0244954 A1 | 11/2005 | Blackburn et al. |
| 2005/0245690 A1 | 11/2005 | Rajagopalan et al. |
| 2005/0260118 A1 | 11/2005 | Lu et al. |
| 2005/0277710 A1 | 12/2005 | Joyce et al. |
| 2006/0025524 A1 | 2/2006 | Schneider et al. |
| 2006/0029811 A1 | 2/2006 | Sugioka et al. |
| 2006/0223965 A1 | 10/2006 | Trifu |

FOREIGN PATENT DOCUMENTS

| | | |
|---|---|---|
| EP | 1 254 372 | 6/2004 |
| EP | 1 283 195 | 10/2005 |
| EP | 1 118 090 | 11/2005 |
| EP | 1 171 496 | 12/2005 |
| JP | 2002537502 | 11/2002 |

| JP | 2007512211 | 5/2007 |
| JP | 2007528451 | 10/2007 |
| WO | WO 97/43116 | 11/1997 |
| WO | 99/21654 | 5/1999 |
| WO | 99/67425 | 12/1999 |
| WO | WO 00/19461 | 4/2000 |
| WO | WO 00/50349 | 8/2000 |
| WO | 00/56795 | 9/2000 |
| WO | 01/35100 | 5/2001 |
| WO | 01/62232 | 8/2001 |
| WO | 02/17883 | 3/2002 |
| WO | 02/32588 | 4/2002 |
| WO | WO 02/46130 | 6/2002 |
| WO | WO 03/054146 | 7/2003 |
| WO | 03/075888 | 9/2003 |
| WO | WO 03/084980 | 10/2003 |
| WO | 2004/022121 | 3/2004 |
| WO | 2004/024201 | 3/2004 |
| WO | WO 2004/037714 | 5/2004 |
| WO | 2004/053205 | 6/2004 |
| WO | 2004/065295 | 8/2004 |
| WO | WO 2004/072104 | 8/2004 |
| WO | 2004/076056 | 9/2004 |
| WO | 2004/078641 | 9/2004 |
| WO | 2004/096944 | 11/2004 |
| WO | 2004/099068 | 11/2004 |
| WO | 2004/103319 | 12/2004 |
| WO | WO 2005/000483 | 1/2005 |
| WO | WO 2005/002662 | 1/2005 |
| WO | 2005016824 | 2/2005 |
| WO | WO 2005/023700 | 3/2005 |
| WO | 2005035238 | 4/2005 |
| WO | WO 2005/033001 | 4/2005 |
| WO | 2005/047467 | 5/2005 |
| WO | WO 2005/044723 | 5/2005 |
| WO | 2005052591 | 6/2005 |
| WO | WO 2005/049707 | 6/2005 |
| WO | 2005066286 | 7/2005 |
| WO | WO 2005/075340 | 8/2005 |
| WO | 2005/082277 | 9/2005 |
| WO | 2005/089825 | 9/2005 |
| WO | 2005082277 | 9/2005 |
| WO | WO 2005/084582 | 9/2005 |
| WO | WO 2005/084805 | 9/2005 |
| WO | WO 2005/087673 | 9/2005 |
| WO | 2005/100633 | 10/2005 |
| WO | 2005/100642 | 10/2005 |
| WO | WO 2005/113431 | 12/2005 |

OTHER PUBLICATIONS

XP-002469484 Larsen,Gustavo, et al. "A Method for Making Inorganic and Hybrid Fibers and Vesicles . . . ," Journal of American Chemistry Society, pp. 1154-1155, Jan. 7, 2003.

XP-019212805 Moreau, Joel, J.E., et al. "New Approach for the Organisation and the Shaping . . . ," Journal of Sol-Gel Science and Technology, vol. 31, pp. 151-156 (2004).

XP-002443403 Nunes, S.C., et al. "Structure and photoluminescent features of di-amide cross-linked alkylene-siloxane hybrids," J. Mat. Chem, vol. 15, pp. 3876-3886 (2005).

International Search Report (15 pgs.).

Granqvist, "Biodegradable and bioactive hybrid organic-inorganic PEG-siloxane fibers", Colloid Polymer Science, 2004, vol. 282, pp. 495-501.

Sung-Seen, "Silica nanofibers from electrospinning/sol-gel process", Jn. of Materials Science Letters, 2003, vol. 22, pp. 891-893.

Honma, "Synthesis of organic/inorganic nanocomposites protonic conducting membrane through sol-gel processs", Solid State Ionics, 1999, vol. 118, pp. 29-36.

Honma, "Protonic conducting properties of sol-gel derived organic/inorganic nanocomposite membranes doped with acidic . . . ", Solid State ionics, 1999, vol. 120, pp. 255-264.

Honma, "Protonic conducting organic/inorganic nanocomposites for polymer electrolyte membrane", Jn of Membrane Science, 2001, vol. 185, pp. 83-94.

Grafe, "Nanofiber Webs from Electrospinning", Nonwovens in Filtration 5th Intl Conference, 2003.

European Office Action in related European Patent Application No. 06850594.0. Jun. 6, 2012. 4 pgs.

European Office Action in related European Patent Application No. 06850594.0. Jun. 21, 2011. 9 pgs.

Huang, "Structure-property behaviour of hybrid materials incorporating tetraethoxysilane with multifunctional poly (tetramethylene oxide)",Polymer,Nov. 1989,v.30 n 11,p. 2001-2012.

Young, "Covalent and non-covalently coupled polyester-inorganic composite materials", Polymer, 2002, vol. 43, pp. 6101-6114.

Zea Bermudez, V., et al., "Sol-gel derived urea cross-linked organically modified silicates", Chem. Mater., 1999, vol. 11, pp. 569-580.

Yano, "Physical properties and structure of organic-inorganic hybrid materials produced by sol-gel process", Materials Science & Engineering, Nov. 1998, vol. 6 n2-3, pp. 75-90.

Gomes Correia, S.M., et al., "Sol-gel-derived POE/siliceous hybrids doped with Na+ ions: Morphology and ionic . . . ", Solid State Ionics, Jan. 2003, vol. 156 n 1-2, pp. 85-93.

Bounor-Legare, "New transesterification between ester and alkoxysilane groups:application to ethylene-co-vinyl acetate copolymer crosslinking",Polymer,2002,vol. 43, p. 6085-6092.

Bounor-Legare, "A new route for organic-inorganic hybrid material synthesis through reactive processing without solvent", Polymer, 2004, vol. 45, pp. 1485-1493.

XP-002449175, Database CA [Online], Chem. Abstr. Service, Entered CAPLUS Nov. 23, 2005, Joubert, Mathieu, et al. "Synthesis of poly(.vepsiln-caprolactone)-silica . . . ". pp. 1-3.

XP-002449176, Database CA [Online], Chem. Abstr, Service, Entered CAPLUS Dec. 19, 2005. Boutti, Salima et al. "Silica/polyamide nanocomposite synthesis via an . . . ". pp. 1-2.

XP-002449177, Database CA [Online], Chem. Abstr. Service, Donley, M.S. et al. "The self-assembled nanophase particle (SNAP) process: a nanoscience . . . ". Dec. 12, 2003. pp. 1-2.

International Search Report corresponding to International Patent Application PCT/US06/048574, mailing date May 10, 2007.

International Search Report corresponding to International Patent Application PCT/US06/048575, mailing date Sep. 17, 2007.

* cited by examiner

SPUN NANOFIBER, MEDICAL DEVICES, AND METHODS

BACKGROUND OF THE DISCLOSURE

Nanotechnology is an emerging field that uses the principles of science and engineering to fabricate materials or structures of dimensions in the nanometer scale. The nanoscale materials can display unusual and unique property profiles as compared to macromaterials. Physical, chemical and biological properties such as unique shape, orientation, surface chemistry, topology and reactivity exhibited by these materials originate from their small dimensions. These material properties can translate into unusual electrical, optical, magnetic, mechanical, thermal and biological properties for these materials.

Some nanostructures or nanoscale materials currently under investigation include quantum dots and wires, nanoscale self-assemblies and thin films, nanocrystals, nanotubes, nanowires, nanorods, nanofoams, nanospheres and nanofibers. Among these nanostructures, nanofibers form one of the most extensively investigated areas. The word nanofiber refers to fibrous structures usually made of carbon, organic polymers or organometallic polymers with diameter less than one micrometer. Nanofibers can be fabricated using various processing techniques such as drawing, self assembly, template synthesis, phase separation, dry spinning, and electrospinning.

Currently medical device catheters, and other types of medical devices where a smaller size is preferred, have a need to further reduce size and mass. This reduction in size and mass may allow for enhanced product performance leading to minimized patient trauma and recovery time. Attempts have been made to incorporate nanofibers into polymer matrices for the purpose of improving both the durability and surface characteristics (e.g., abrasion resistance) of the polymer. However, traditional nanofibers typically need to be surface treated with additional compounds in order to prevent their conglomeration during the electrospinning process and/or processed with or mixed into the base polymer material. A suitable solution to this problem is desired.

DETAILED DESCRIPTION OF DISCLOSURE

The present disclosure provides compounds from which nanofibers can be produced, the resulting nanofibers produced from the compounds, and nanofiber reinforced polymers prepared using the nanofibers and a polymer. The compounds used in forming the nanofibers include chemical linkage moieties that are capable of forming non-covalent bonds with portions of the polymer so as to form the nanofiber reinforced polymers. This interaction allows the nanofibers to be integrated with the polymer without conglomerating or clumping as could occur with nanofibers without such non-covalent bonding interactions. Because of their small diameters, electrospun nanofibers have larger surface-to-volume ratios, which enable them undergo a greater extent of non-covalent bonding with a polymer, as compared to larger diameter fibers.

The nanofibers of the present disclosure can be incorporated into the polymer so as to form the nanofiber reinforced polymers in a variety of ways. For example, the nanofibers can be formed on and/or applied to a surface of the polymer, where the nanofiber can non-covalently bond to the polymer due to the presence of the chemical linkage moieties in the nanofibers and the corresponding non-covalent bonding groups in portions of the polymer. Alternatively, the nanofibers of the present disclosure can be incorporated into (i.e., embedded into) the polymer so as to be essentially surrounded by the polymer in forming the nanofiber reinforced polymers. The nanofibers can function, besides other things, to provide reinforcement to the polymer allowing for a reduced size and mass for the medical device.

The nanofiber reinforced polymers of the present disclosure can be suitable for use as a biomaterial and/or in medical devices. The nanofiber(s) and the polymer each include chemical linkage moieties capable of forming non-covalent bonds that allow the components of the nanofiber reinforced polymers to display excellent performance in many characteristics important for medical device use, including compressive strength, diametral tensile strength, flexural strength, fracture toughness, puncture resistance, hardness, changes in hydrophobicity, adhesion, non-adhesion, friction, patency or biointegration of the device with one or more tissue surfaces of a body of a patient depending on the particular application of the device, resistance to wear (e.g., characterized by compressive strength and diametral tensile strength), durability, thermal expansion, visual opacity, x-ray opacity, impact strength, chemical durability, electrical conductivity, biocompatibility, modulus, shelf life, patient comfort, ease-of-use, and structural integrity relative to a polymer without the nanofiber reinforcement of the silicon oxide based polymer of the present disclosure.

As used herein, "nanofiber reinforced polymers" refer to a polymer that contains, at least in part, nanofibers of a silicon oxide based polymer formed from the compound of the present disclosure that interact with the polymer and any desired filler and/or adjuvants. Nanofiber reinforced polymers of the present disclosure can be multiple- or one-part compositions, as will be discussed herein.

In addition, the nanofiber reinforced polymers of the present disclosure can be further characterized in that they are substantially insoluble in body fluids and tissues and are designed and constructed to be placed in or onto the body or to contact fluid or tissue of the body. Ideally, the nanofiber reinforced polymers will be biostable, biocompatible, and will not induce reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized; and will substantially maintain its physical properties and function during the time that it remains implanted in or in contact with the body. A "biostable" material is one that is not broken down by the body, whereas a "biocompatible" material is one that is not rejected by the body.

As used herein, a "medical device" can be defined as a device that has surfaces that contact blood or other body fluids and/or tissues in the course of their operation. This can include, for example, extracorporeal devices for use in surgery such as blood oxygenators, blood pumps, blood sensors, tubing used to carry blood and the like which contact blood which is then returned to the patient. This can also include devices such as vascular grafts, stents, electrical stimulation leads, valves for use in the cardiac system (e.g., heart valves), orthopedic devices, intracorporeal or extracorporeal devices (e.g., catheters), catheter shaft components, filters, guide wires, shunts, clamps, sensors, membranes, balloons (e.g., angioplasty balloons), anastomotic devices, aneurysm repair devices, embolic devices, implantable devices (e.g., orthopedic implants), replacement devices for nucleus pulposus, cochlear or middle ear implants, intraocular lenses, coatings for such devices, and the like that comprise nanofiber reinforced polymers.

Nanofiber reinforced polymers of the present disclosure can be used in medical devices as well as nonmedical devices. As discussed, they can be used in medical devices and are suitable as biomaterials. Examples of medical devices are listed herein. Examples of nonmedical devices include foams, insulation, clothing, footwear, paints, coatings, adhesives, and building construction materials, besides others.

As used herein, chemical linkage moieties capable of forming a "non-covalent bond" include those that are capable of forming a chemical bond that allows for non-bonded interactions due to van der Waals, electrostatic, and/or hydrogen bonding forces. For example, chemical linkage moieties capable of forming a "non-covalent bond" include those that can form hydrogen bonds such as, but not limited to, urethanes, amides, esters, and combination thereof.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups). In the context of the present disclosure, suitable organic groups of this disclosure are those that do not interfere with the formation of the nanofibers and the nanofiber reinforced polymers.

In the context of the present disclosure, the term "aliphatic group" means a saturated or unsaturated linear or branched hydrocarbon group. This term is used to encompass alkyl (e.g., $-CH_3$, which is considered a "monovalent" group) (or alkylene if within a chain such as $-CH_2-$, which is considered a "divalent" group), alkenyl (or alkenylene if within a chain), and alkynyl (or alkynylene if within a chain) groups, for example. The term "alkyl group" means a saturated linear (i.e., straight chain), cyclic (i.e., cycloaliphatic), or branched monovalent hydrocarbon group including, for example, methyl, ethyl, n-propyl, isopropyl, t-butyl, amyl, heptyl, dodecyl, octadecyl, 2-ethylhexyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. These hydrocarbon groups can be substituted with heteroatoms, which can be in the form of functional groups. The term "heteroatom" means an element other than carbon (e.g., fluorine, nitrogen, oxygen, sulfur, chlorine, etc.).

As a means of simplifying the discussion and the recitation of certain terminology used throughout this disclosure, the terms "group" and "moiety" are used to differentiate between chemical species that allow for substitution or that can be substituted and those that do not so allow for substitution or can not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

As used herein, the terms "a," "an," "the," "one or more," and "at least one" are used interchangeably and include plural referents unless the context clearly dictates otherwise. Thus, for example, reference to "a nanofiber" optionally includes a plurality of such nanofibers, and the like. Unless defined otherwise, all scientific and technical terms are understood to have the same meaning as commonly used in the art to which they pertain. For the purpose of the present invention, additional specific terms are defined throughout.

The term "nanofiber" as used herein, refers to a nanostructure typically characterized by at least one physical dimension less than about 1000 nm, less than about 500 nm, less than about 250 nm, less than about 150 nm, less than about 100 nm, less than about 50 nm, less than about 25 nm or even less than about 10 nm or 5 nm. In many cases, the region or characteristic dimension will be along the smallest axis of the structure. In addition, nanofibers typically have one principle axis that is longer than the other two principle axes and, thus, have an aspect ratio greater than one, an aspect ratio of 2 or greater, an aspect ratio greater than about 10, an aspect ratio greater than about 20, or an aspect ratio greater than about 100, 200, or 500.

It will be appreciated that the term nanofiber can optionally include such structures as, e.g., nanowires and nanowhiskers.

In certain embodiments, nanofibers herein have a substantially uniform diameter. In some embodiments, the diameter shows a variance less than about 20%, less than about 10%, less than about 5%, or less than about 1% over the region of greatest variability and over a linear dimension of at least 5 nm, at least 10 nm, at least 20 nm, or at least 50 nm. For example, a wide range of diameters could be desirable due to cost considerations and/or to create a more random surface. Typically the diameter is evaluated away from the ends of the nanofiber (e.g. over the central 20%, 40%, 50%, or 80% of the nanofiber). In yet other embodiments, the nanofibers herein have a non-uniform diameter (i.e., they vary in diameter along their length).

The present disclosure relates to a nanofiber formed from at least one silicon alkoxide having a chemical linkage moiety that can form a non-covalent bond for interaction with a polymer. These compounds are of the formula (Formula I):

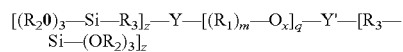

where each $R_1$, $R_2$ and $R_3$ can be the same or different (i.e., is independently) an organic group. Examples of such organic groups include a straight chain or branched alkyl group, a straight chain or branched alkylene group, where each $R_1$, $R_2$ and $R_3$ optionally includes heteroatoms that can be in the chain of the organic group or pendant therefrom as in a functional group. X and z are each independently 0 or 1; m is 1 to 18; and q is 1 to 200. Y and Y' are the chemical linkage moieties that can form a non-covalent bond with a portion of a polymer, where Y and Y' are selected together from the group consisting of:

—NH—(C=O)—O— for Y and —(C=O)—NH— for Y', where z=1

—NH—(C=O)— for Y and —(C=O)—NH— for Y', where x=0 and z=1

—O—(C=O)— for Y and —(C=O)— for Y', where z=1

—(NR$_4$)—(C=O)—(NH)— for Y and Y', where z=1; and

—N—[CH$_2$—(CHOH)—CH$_2$—O—R$_3$—Si—(OR$_2$)$_3$]$_2$ for Y and Y', where z=0.

In one embodiment, the values for m, x, and q, and R$_1$, R$_2$ and R$_3$ groups are selected such that the number average molecular weight of a compound of Formula I is suitable to allow for subsequent melt processing with one or more polymers, as discussed herein.

In one embodiment, each R$_1$ is independently a straight chain or branched alkylene group optionally including heteroatoms, such as nitrogen, oxygen, phosphorus, sulfur, and halogen. The heteroatoms can be in the backbone of the R$_1$ or pendant therefrom, and they can form functional groups. Such heteroatom-containing groups (e.g., functional groups) include, for example, an alcohol, carbonyl, ether, acetoxy, ester, aldehyde, acrylate, amine, amide, imine, imide, and nitrile, whether they are protected or unprotected. In one embodiment, R$_1$ does not include heteroatoms. In an additional embodiment, each R$_1$ is independently a straight chain or branched alkylene group includes 18 carbon atoms or less. In a further embodiment, each R$_1$ is independently a straight chain or branched (C2-C8)alkylene group. In other embodiments, each R$_1$ is independently a straight chain or branched (C2-C4)alkylene group (e.g., ethylene, n-propylene, isopropylene, or butylene). In one example, R$_1$ is a C3 alkylene group (propylene or isopropylene).

In an alternative embodiment, when m=1, q=1 and x=0 and R$_1$ can be selected from groups consisting of polypropylene, polyurethane, fluoropolymer (e.g., polytetrafluoroethylene), polyester, polyethylene, polyvinyl chloride, polyamide, and polyimide.

In one embodiment, each R$_2$ and R$_4$ is independently a straight chain or branched alkyl group optionally including heteroatoms, such as nitrogen, oxygen, phosphorus, sulfur, and halogen. The heteroatoms can be in the backbone of R$_2$ and/or R$_4$ or pendant therefrom, and they can form functional groups. Such heteroatom-containing groups (e.g., functional groups) include, for example, an alcohol, carbonyl, ether, acetoxy, ester, aldehyde, acrylate, amine, amide, imine, imide, and nitrile, whether they are protected or unprotected. In one embodiment, R$_2$ and/or R$_4$ do not include heteroatoms. In an additional embodiment, each R$_2$ and R$_4$ is independently a straight chain or branched alkyl group includes 18 carbon atoms or less. In a further embodiment, each R$_2$ and R$_4$ is independently a straight chain or branched (C2-C8)alkyl group. In other embodiments, each R$_2$ and R$_4$ is independently a straight chain or branched (C2-C4)alkyl group (e.g., ethyl, n-propyl, isopropyl, or butyl). In one example, R$_2$ and R$_4$ are each a C2 alkyl group.

In one embodiment, each R$_3$ is independently a straight chain or branched alkylene group optionally including heteroatoms, such as nitrogen, oxygen, phosphorus, sulfur, and halogen. The heteroatoms can be in the backbone of R$_3$ or pendant therefrom, and they can form functional groups Such heteroatom-containing groups (e.g., functional groups) include, for example, an alcohol, carbonyl, ether, acetoxy, ester, aldehyde, acrylate, amine, amide, imine, imide, and nitrile, whether they be protected or unprotected. In one embodiment, R$_3$ does not include heteroatoms. In an additional embodiment, each R$_3$ is independently a straight chain or branched alkylene group includes 18 carbon atoms or less. In a further embodiment, each R$_3$ is independently a straight chain or branched (C2-C8)alkylene group. In other embodiments, each R$_3$ is independently a straight chain or branched (C2-C4)alkylene group (e.g., ethylene, n-propylene, isopropylene, or butylene). In one example, R$_3$ is a C3 alkylene group (propylene or isopropylene).

As will be appreciated, for the formulas herein, R$_1$, R$_2$, and R$_3$ can vary within any one molecule. For example, in addition to each R$_1$, R$_2$, and R$_3$ being the same or different within each [(R$_2$O)$_3$—Si—R$_3$]z-Y—[(R$_1$)$_m$—O$_x$]$_q$—Y'—[R$_3$—Si—(OR$_2$)$_3$]$_z$ group, the (R$_1$)$_m$—O$_x$ groups can be the same or different in any one molecule.

The compounds of Formula I: [(R$_2$O)$_3$—Si—R$_3$]$_z$—Y—[(R$_1$)$_m$—O$_x$]$_q$—Y'—[R$_3$—Si—(OR$_2$)$_3$]$_z$ are capable of being formed, either alone or with other precursor compounds (e.g., at least one silicon alkoxide), into a cross-linked network of a silicon oxide based polymer from which nanofibers and/or nanofiber reinforced polymers can be formed, as discussed herein. Although certain compounds are described herein, the compounds used to form the nanofiber and the nanofiber reinforced polymers of the present disclosure can be formed from a wide variety of compounds having chemical groups that can form chemical linkage moieties capable of forming non-covalent bonds. For example, a method of preparing the nanofibers from the compounds of Formula I involves the combining of (1) at least one compound of the formula (Formula II) RO$_f$—(C=O)$_i$—[(R$_1$)$_m$—O$_x$]$_q$(C=O)$_n$—O$_e$—R and (2) at least one alkoxy silane containing compound of the formula (Formula III) (R$_2$O)$_3$Si(R$_3$-A) that can react to form the compound of Formula I: [(R$_2$O)$_3$—Si—R$_3$]$_z$—Y—[(R$_1$)$_m$—O$_x$]$_q$—Y'—[R$_3$—Si—(OR$_2$)$_3$]$_z$, as discussed herein, and (3) preparing nanofibers from a solution of a cross-linked network from at least one compound of Formula I.

For the compound of Formula II, i, n, x, e and f are each independently 0 or 1; each R is independently H, an amine (e.g., a primary amine and/or a secondary amine), an isocyanate, or an organic group, R$_1$ is an organic group, as discussed herein, m is 1 to 18, and q is 1 to 200, as discussed herein. For the compound of Formula III, R$_2$ and R$_3$ are each independently an organic group, as discussed herein. Each A is independently a hydroxyl (—OH), an isocyanate, an amine (e.g., a primary amine and/or a secondary amine), or an epoxy compound, selected based upon the value of i, n, e and f, and the group selected for R.

In one embodiment, when R is an organic group it can be a straight chain or branched alkyl group optionally including heteroatoms, such as nitrogen, oxygen, phosphorus, sulfur, and halogen. The heteroatoms can be in the backbone of the R, or pendant therefrom, and they can form functional groups. Such heteroatom-containing groups (e.g., functional groups) include, for example, an alcohol, carbonyl, ether, acetoxy, ester, aldehyde, acrylate, amine, amide, imine, imide, and nitrile, whether they are protected or unprotected. In one embodiment, R does not include heteroatoms. In an additional embodiment, R is a straight chain or branched alkyl group includes 18 carbon atoms or less. In a further embodiment, R is a straight chain or branched (C2-C18)alkyl group. In other embodiments, R is a straight chain or branched (C2-C8)alkyl group (e.g., ethyl, n-propyl, isopropyl, butyl, pentyl, hexyl, hepyl, or octyl). In one example, R is a C2 alkyl group.

Examples of nanofibers can be prepared from an amine-containing compounds of Formula III where A is either a primary amine (—NH$_2$) or a secondary amine (—NH)—R), and the compound of Formula II having at least one functional group reactive with the amine group of Formula III, such as an acid, to form an amide for the chemical linkage moiety. In an additional embodiment, one could react the amine group on the compound of Formula III with an anhydride group on the compound of Formula II to make an imide for the chemical linkage moiety. Alternatively, one could react the amine group on the compound of Formula III with an isocyanate group on the compound of Formula II to make a ureylene for the chemical linkage moiety.

In addition, nanofibers can be prepared from a hydroxyl containing compounds of Formula III and the compound of Formula II having at least one functional group reactive with the hydroxyl group of Formula III, such as an acid, to form an ester for the chemical linkage moiety. Alternatively, the nanofibers can be prepared from an amine containing compounds of Formula II (e.g., R is an amine) and the compound of Formula III having at least one functional group reactive with the amine group of Formula II, such as an epoxy compound for A, to form a compound having one or more cabocationic species, such as carbenium ions and/or alkanium ions for the chemical linkage moiety. For example, group A in Formula III can have an epoxy structure, such as

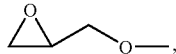

that is reactive with the amine group of Formula II.

Nanofibers can also be prepared from compounds of Formula III, where A is an isocyanate group, and the compound of Formula II having at least one functional group reactive with the isocyanate group of Formula III, such as an alcohol and/or a primary (i.e., —NH$_2$) or secondary amine (i.e., —(NH)—R) to form a urethane and/or a urea for the chemical linkage moiety, Y and Y' in Formula I.

In one example, a urethane- and/or a urea-linkage containing compound of the formula (Formula I): [(R$_2$O)$_3$—Si—R$_3$]$_x$—Y—[(R$_1$)$_m$—O$_x$]$_q$—Y'—[R$_3$—Si—(OR$_2$)$_3$]$_x$, where Y and Y' provide the urethane- and/or a urea linkage, are made using an isocyanate-containing compound of Formula III (R$_2$O)$_3$Si(R$_3$-A). It should be understood, however, that a variety of polyols and/or polyamines can be used, including polyester, polyether, and polycarbonate polyols, for example. Furthermore, the polyols and polyamines can be aliphatic (including cycloaliphatic) or aromatic, including heterocyclic compounds, or combinations thereof.

Suitable polyols for use as the compound of Formula II include polyalkylene oxides (e.g., polyethylene oxide and polybutylene oxide), polypropylene ether glycols, polytetramethylene ether glycols (e.g., PTMEG sold under the trade designators "POLYMEG" or "Terathane"), polycaprolactone diols, and polyester polyols (e.g., hydroxyl terminated polyesters obtained from esterification of dicarboxylic acids and diols.

Examples of suitable isocyanate-containing compounds of Formula III (R$_2$O)$_3$Si(R$_3$-A) for preparation of urethane or urea linkage containing nanofibers from the compound of Formula I are typically aliphatic monoisocyantes, diisocyantes and triisocyantes, or combinations thereof. In addition to the isocyanate groups they can include other functional groups such as biuret, urea, allophanate, uretidine dione (i.e., isocyanate dimer), and isocyanurate, etc., that are typically used in biomaterials. In one example, the isocyanate-containing metalloid alkoxide can be 3-(triethoxysilyl)propyl isocyanate (Sigma-Aldrich, Milwaukee, Wis.).

The present disclosure further provides methods of preparing a nanofiber from the compound of Formula I, as discussed herein. In one embodiment, methods of preparing the nanofiber can include forming a cross-linked network from at least one compound of Formula I using a sol-gel process. The nanofiber can then be produced from a solution of the cross-linked network through a spinning process, such as dry-spinning and/or electrospinning. The nanofiber can then be applied to and/or incorporated into a polymer having a functional group that can non-covalently bond with the chemical linkage moities of the nanofibers to form the biomaterial of the present disclosure. Surprisingly, the nanofibers of the present disclosure can be integrated with and/or into the polymer of the biomaterial so as to provide reinforcement to the biomaterial.

Although certain compounds capable of forming nanofibers are described herein, the nanofibers of the present disclosure can be formed from a wide variety of compound of Formula I. For example, a method of preparing the nanofibers involves (1) providing at least one compound of Formula I; (2) forming a cross-linked network with at least one compound of Formula I; and (3) preparing nanofibers from a solution of a cross-linked network with at least one compound of Formula I.

In one embodiment, the nanofibers are formed from a cross-linked network with the silicon oxide based polymer (i.e., the compound discussed herein) formed through, for example, a sol-gel process. In one embodiment, the cross-linked network of the silicon oxide based polymer used to form the nanofibers is provided in a solution from which the nanofibers can be spun.

The Sol-gel process is generally described, for example, in "Sol-Gel Science: The Physics and Chemistry of Sol-Gel Processing" (Brinker et al., Academic Press, 1990). As used herein, "sol-gel" refers to methods of forming the cross-linked network of the silicon oxide based polymer formed from the compound of Formula I that involves the evolution of inorganic networks through the formation of a colloidal suspension (sol) and gelation of the sol to form a network in a continuous phase (gel).

Three reactions are generally used to describe the sol-gel process: hydrolysis, alcohol condensation, and water condensation. The characteristics and properties of the cross-linked network formed throughout the sol-gel process can be related to a number of factors that affect the rate of hydrolysis and condensation reactions, such as, pH, temperature and time of reaction, reagent concentrations, catalyst nature and concentration, aging temperature and time, and drying. Controlling these factors allow for the structure and properties of the sol-gel-derived cross-linked network formed from the compound to be varied as desired.

A method for preparing the cross-linked network for the present disclosure through a sol-gel process involves the combining of (1) at least one of the compound of the present disclosure and (2) an aqueous or organic dispersion or sol of reagents that include at least one alcohol and a catalyst provided under conditions for the sol-gel reaction to take place.

Examples of suitable catalysts include mineral acids such as hydrochloric acid (HCl), ammonia, acetic acid, potassium hydroxide (KOH), titanium alkoxides, vandium alkoxides, amines, KF, and HF. Additionally, it has been observed that the rate and extent of the hydrolysis reaction is most influenced by the strength and concentration of the acid- or base catalyst. In one embodiment, the concentration of the acid- or base catalyst can be from 0.01 M to 7M. In addition, the nature of the cross-linked network can be influenced by the selection of an acid or base catalyst, where under acid-catalyzed conditions the cross-linked network yields primarily linear or randomly branched polymers which entangle and form additional branches resulting in gelation. On the other hand, cross-linked network derived under base-catalyzed conditions can yield more highly branched clusters which do not interpenetrate prior to gelation and thus behave as discrete clusters.

Examples of suitable alcohols include anhydrous alcohol such as methanol, ethanol, propanol, butanol, pentanol, and mixtures thereof. Suitable alcohols have a water content of less than about 1% by weight, especially less than about 0.5% by weight or less than about 0.1% by weight. Other organic solvent (or mixtures of solvents) can also be used that are miscible with the other components.

According to the present disclosure, the sol-gel reaction can take place with the reagents in a liquid phgase. Typical reaction conditions for the sol-gel reaction can occur in a temperature range of 20° C. through 100° C. Other temperature ranges are also possible.

The present disclosure also provides for forming the nanofibers from the compounds of Formula I that can be used in biomaterials to form medical devices. Methods of preparing the compound of Formula I, a cross-linked network of at least one compound of Formula I, and preparing the nanofiber from a solution of the cross-linked network are also provided. The compounds of Formula I can be made through an end-capping reaction that forms the chemical linkage moieties (e.g., Y and Y') that can form a non-covalent bond with portions of the polymer and an endcap of a silicon alkoxide.

In a typical end-capping reaction, the compound(s) of Formula II, as described herein, and at least one silicon containing compound of Formula III are combined in the presence of a suitable solvent, and optionally additives to control the chemical and thermal stability of the end-capping reaction. An example of a suitable solvent includes tetrahydrofuran (THF). An example of a suitable additive includes monophenyltriethoxysilane (MPH). The reactions typically take place under reflux conditions (e.g., temperature range of 20 to 80° C.) in an inert atmosphere (e.g., under nitrogen) for a time sufficient for the reaction to come to completion.

The one or more compounds can then be processed to cross-link the compounds prior to forming the nanofibers. An example of such a cross-linking process includes the sol-gel process, as discussed herein. Examples, of suitable methods of producing nanofibers according to the present disclosure include one or more spinning techniques from a solution of the cross-linked network in an appropriate solvent(s). For example, an electrospinning process is used to produce the desired nanofibers. Alternatively, a dry-spinning process is used to produce the desired nanofibers.

In electrospinning, a solution of the cross-linked network of at least one compound of Formula I is subjected to an electrical potential as the solution is continually pumped into spinnerets or a spray cannula. The spinnerets or the spray cannula is separated some distance from a counterelectrode (target) of opposite polarity to establish a static electric field. The counterelectrode can typically be in the form of a metal screen, plate, or rotating mandrel.

As the charged solution is pumped from the spinnerets or a spray cannula a so-called "Taylor Cone" forms due to the competing forces of the static electric field and the solution's surface tension. In the present disclosure, the solution includes the cross-linked polymer in solution and the concentration of that cross-linked polymer is sufficiently high to cause molecular chain entanglement so as to allow a fiber to be drawn from the tip of the Taylor Cone. Field strengths for the electrical potential (kV) and linear spinning speeds (exit speed at spinneret in m/s) and weight percentage of cross-linked polymers in solution (e.g., in a volatile organic solvent or solvent mixture) can be determined for each individual cross-linked polymers in solution. Examples of possible solvents include, but are not limited to, dimethyl ether, dichloromethane, chloroform, ethylene glycol dimethyl ether, ethylglycol isopropyl ether, ethyl acetate or acetone or a mixture thereof with or without further solvents.

During the nanofiber's travel from the spinnerets or spray cannula to the counterelectrode, the solvent gradually evaporates, and a charged nanofiber is left to accumulate on the coutnterelectrode. The charge on the nanofibers eventually dissipates into the surrounding environment. In one embodiment, the resulting product is a non-woven fiber mat that is composed of the nanofibers of the present disclosure. It is also possible for the counterelectrode to be moved with respect to the nozzle position, which allows for specific fiber orientations (parallel alignment or random) to be achieved. The mechanical properties of the scaffold can be varied by varying the fiber diameter and orientation. It is also possible for the nanofibers to be collected on spools for forming yarns and/or woven textiles, as discussed herein.

The vaporizing step may be carried out at atmospheric pressure or else under reduced pressure. If necessary, the pressure shall be adapted to the boiling points of the solvents.

The nanofibers of the present disclosure can also be produced through a dry-spinning process that is carried out in a spinning column. The temperature of the solution of the cross-linked network in the volatile organic solvent or solvent mixture can be sufficiently high to allow for rapid evaporation of the solvent as the nanofiber is produced. Extrusion speed (m/min), take-up speed (m/min), and the amount and temperature of the spin gas ($m^3$/h) used conforming with known practices can be applied. The tow leaving the dry-spinning column and obtained in the manner described can be wound on spools or stored for after treatment.

The nanofibers produced by the process of the present disclosure can be processed into nonwoven fibrous assemblies or into linear assemblies that can include weaving, braiding or knitting into 2-dimensional and 3-dimensional configurations. The degree of complexity for the nonwoven fibrous assemblies and/or the linear assemblies can depend in part upon, e.g., the length of the nanofibers, the diameter of the nanofibers, the length:diameter aspect ratio of the nanofibers, and the growth conditions of the nanofibers. Thus, it will be appreciated that the utility of the nanofibers herein is optionally controlled through manipulation of these and other parameters.

The nanofibers can also be wet-chemically and plasma-chemically modified, or loaded with materials having different objectives, for example pharmaceutically active entities or catalytic precursors, by impregnating and subsequent drying. Surface modification may be used to confer on the nanofibers a more hydrophilic or hydrophobic surface, and this is advantageous for use in the biological or biomedical sector. In an additional embodiment, the nanofibers may be stiffened by sintering the fibers together (or otherwise cross-linking the fibers, e.g., by chemical means) prior to or after incorporating the nanofibers into or onto the polymer to provide enhanced rigidity and strength.

In one embodiment, the nanofibers according to the present disclosure can be used as reinforcing composite components in the nanofiber reinforced polymers of the present disclosure. In addition, the nanofibers in the nanofiber reinforced polymers can also be used to enhance the durability and resistance to wear. Of course, it will be appreciated that the current invention is not limited by recitation of particular nanofiber and/or polymer compositions, and that, unless otherwise stated, any of a number of other materials are optionally used in different embodiments herein. It is to be understood that this invention is not limited to particular configurations, which can, of course, vary (e.g., different combinations of nanofibers and substrates and optional moieties, etc. which are optionally present in a range of lengths, densities, etc.).

The nanofibers of this invention can be substantially homogeneous in material properties, or in certain embodiments they are heterogeneous (e.g. nanofiber heterostructures). As will be appreciated, the nanofibers of the present disclosure can, thus, be composed using any of a myriad of possible compounds of Formula I (or combinations thereof). Some embodiments herein comprise nanofibers composed using one or more compounds of Formula I. Any recitation of specific nanofiber compositions herein should not be taken as limiting.

Additionally, the nanofibers of the invention are optionally constructed through any of a number of different methods, and examples listed herein should not be taken as limiting. Thus, nanofibers constructed through means not specifically described herein, but which fall within the parameters as set forth herein are still nanofibers of the invention and/or are used with the methods of the invention.

The present disclosure also provides nanofiber reinforced polymers and medical devices comprising such nanofiber reinforced polymers, as well as methods and uses for such nanofiber reinforced polymers and medical devices. In one embodiment, the nanofibers of the present disclosure may be spun and/or applied on or to a surface of a polymer having a desired shape, where the polymer includes functional groups that can non-covalently bond with chemical linkage moities of the nanofibers.

Such enhanced interactivity is generally provided by providing a nanostructure surface that interacts with the surface of the polymer to promote integration therewith or attachment thereto. The nanofibers can either be attached to the polymer by growing the nanofibers directly on the surface(s) of the polymer, or by embedding the nanofibers into the polymer of the medical device itself to enhance the rigidity and strength of the medical device. The shape and size of the nanofibers as well as their density on the graft surfaces can be varied to tune the material properties of the medical device to the desired levels.

In an alternative embodiment, the nanofibers can be collected on a surface of a mold having a desired shape for a resulting medical device. Once the nanofibers are collected on the mold surface, the polymer can then be at least partially molded around the nanofibers to form the biomaterial and the resulting medical device. As will be discussed herein, examples of such molding techniques can be selected from blow molding, injection molding, extrusion, casting, and coating. In these embodiments, the nanofibers can act as reinforcing elements to the polymer.

The resulting nanofiber formed from the cross-linked network can provide both mechanical and surface properties, as discussed herein, for the resulting biomaterial. As a result, the biomaterial of the present disclosure can combine the advantages of organic polymers (flexibility, low density, toughness, formability) with the excellent mechanical and surface modification properties of the nanofibers (strength, modulus, etc.).

The medical devices of the present disclosure may also be coated on one or more surfaces with other materials to still further enhance their utility. Examples of suitable coatings are medicated coatings, drug-eluting coatings, hydrophilic coatings, smoothing coatings, collagen coatings, human cell seeding coatings, etc. The above-described nanofiber coatings on the medical device can provide a high surface area that helps the medical device retain these coatings. The coatings can be adsorbed directly to the nanostructure surface of the medical device.

A wide variety of polymers can be used with the present disclosure in forming the nanofiber reinforced polymers. Polymers suitable for use in forming the nanofiber reinforced polymers can include those having sufficient strength, hydrolytic stability, and non-toxicity to render them suitable for use in a biological environment. Polymers used with the nanofibers of the present disclosure can be copolymers, random, alternating, block, star block, segmented copolymers (i.e., containing a multiplicity of both hard and soft domains or segments on any polymer chain), or combinations thereof (e.g., where certain portions of the molecule are alternating and certain portions are random). In addition, polymers of the present disclosure can be linear, branched, or crosslinked.

The polymers suitable for forming the nanofiber reinforced polymers of the present disclosure further include, but are not limited to, chemical linkage moieties that have the ability to form non-covalent bonds. Examples of such polymers include those having urethane, ester, amide, imide, urea, carbonate, sulfone, ether, and/or phosphonates linkages, or combinations thereof. Examples of such polymers include polyamide (nylon), polyurethane, polyureas, polyurethane-ureas, and/or polyester, among others.

In addition, polymers suitable for forming the nanofiber reinforced polymers according to the present disclosure can include both hard and soft segments. As used herein, a "hard" segment is one that is either crystalline (i.e., has ordered domains) at use temperature or amorphous with a glass transition temperature above use temperature (i.e., glassy), and a "soft" segment is one that is amorphous with a glass transition temperature below use temperature (i.e., rubbery). Typically, hard segments add considerable strength and higher modulus to the polymer. Similarly, soft segment adds flexibility and lower modulus, but can add strength particularly if it undergoes strain crystallization, for example. The polymers can vary from hard and rigid to soft and flexible. In one example, the polymers are elastomers. An "elastomer" is a polymer that is capable of being stretched to approximately twice its original length and retracting to approximately its original length upon release.

Suitable polymers can have a viscosity and molecular weights suitable for blending and/or melt processing with the nanofibers, as discussed herein. In addition to the polymers described herein, the nanofiber reinforced polymer of the disclosure can also include a variety of additives. These can include antioxidants, colorants, processing lubricants, stabilizers, imaging enhancers, fillers, and the like. The present disclosure also provides polymers and compounds used to form such polymers, and biomaterials formed from such polymers that can be used in medical devices.

Additional additives can also include, but are not limited to, metal alkoxides $M(OR_2)_n$, where the value for n is dependent on the oxidation state of the metal M. In one embodiment, the metal alkoxides can be incorporated into mixture of Formula I the prior to the sol-gel process. M can be selected from the group of metals consisting of Groups 2, 4, 5, 8, 9, 13, 14 and 15. For example, M can be selected from the group of metals consisting of Si, Fe, Ti, Zr, Ir, Ru, Bi, Ba, Al, Ta, and Sr. In an alternative embodiment, the examples of M elements can include non-metal element C and a polyhedral oligomeric silsesquioxane (POSS). Addition of the additives such as the metal alkoxide can then be used in the sol-gel process to modify the nature of the resulting nanofiber.

The invention has been described with reference to various specific and preferred embodiments. It is understood, however, that there are many extensions, variations, and modification on the basic theme of the present invention beyond that shown in the detailed description, which are within the spirit and scope of the present invention.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments set forth herein and that such embodiments are presented by way of example only with the scope of the disclosure intended to be limited only by the claims set forth herein as follows.

What is claimed is:

1. A biostable nanofiber formed from a compound of the formula (Formula I):

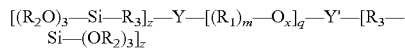

where x and z are each independently 0 or 1; m is 1 to 18; q is 1 to 200; $R_1$, $R_2$ and $R_3$ are each independently an organic group;

and Y and Y' are selected together from the group consisting of:

—O—(C=O)— for Y and —(C=O)— for Y' where z=1;

—($NR_4$)—(C=O)—(NH)— for Y and Y', where z=1, and $R_4$ is an organic group; and —N—[$CH_2$—(CHOH)—$CH_2$—O—$R_3$—Si—($OR_2$)$_3$]$_2$ for Y and Y', where z=0;

where the biostable nanofiber is produced by a spinning process.

2. The nanofiber of claim 1, where the spinning process used to produce the nanofiber is a dry-spinning process.

3. The nanofiber of claim 1, where the spinning process used to produce the nanofiber is an electrospinning process.

4. The nanofiber of claim 1, where the nanofiber is used as a reinforcement component with a polymer to form a biomaterial.

5. The nanofiber of claim 4, where the nanofiber coats the polymer to form the biomaterial.

6. The nanofiber of claim 4, where the nanofiber is embedded in the polymer to form the biomaterial.

7. The nanofiber of claim 4, where the nanofiber includes chemical moieties that can non-covalently bond with portions of the polymer.

8. The nanofiber of claim 1, where the compound of Formula I can form a cross-linked network using a sol-gel process.

9. A medical device prepared from the nanofiber of claim 1.

10. The nanofiber of claim 1, where each $R_1$ and $R_3$ is independently a (C1-C18)alkylene group, and $R_2$ is a (C1-C18)alkyl group.

11. A biostable nanofiber reinforced polymer, comprising:
a polymer; and
nanofibers from a compound of the formula (Formula I):

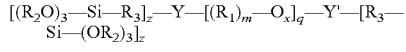

where x and z are each independently 0 or 1; m is 1 to 18; q is 1 to 200; $R_1$, $R_2$ and $R_3$ are each independently an organic group;

and Y and Y' are selected together from the group consisting of:

—O—(C=O)— for Y and —(C=O)— for Y' where z=1;

—($NR_4$)—(C=O)—(NH)— for Y and Y', where z=1, and $R_4$ is an organic group; and —N—[$CH_2$—(CHOH)—$CH_2$—O—$R_3$—Si—($OR_2$)$_3$]$_2$ for Y and Y', where z=0, where the biostable nanofibers include chemical moieties capable of forming a non-covalent bond with portions of the polymer.

12. The reinforced polymer of claim 11, where the nanofibers coat a surface of at least a portion of the polymer.

13. The reinforced polymer of claim 12, where the nanofibers are in a random pattern on the surface of at least a portion of the polymer.

14. The reinforced polymer of claim 11, where the nanofibers are imbedded in at least a portion of the polymer.

15. The reinforced polymer of claim 14, where the nanofibers are in a random pattern imbedded in at least a portion of the polymer.

16. The reinforced polymer of claim 11, where each $R_1$ and $R_3$ is independently a (C1-C18)alkylene group, and $R_2$ is a (C1-C18)alkyl group.

17. The reinforced polymer of claim 11, where the portions of the polymer that can chemically bond with chemical moieties of the metal-oxide based polymer are selected from the group of a urethane, an ester, an amide, an imide, a urea and a combination thereof.

18. The reinforced polymer of claim 11, where the polymer is selected from the group polyamide, polyurethane, polyurea, polyurethane-urea, and polyester.

19. A biomaterial comprising the reinforced polymer of claim 11.

20. A medical device comprising the reinforced polymer of claim 11.

* * * * *